(12) United States Patent
Arndt et al.

(10) Patent No.: US 9,067,890 B2
(45) Date of Patent: Jun. 30, 2015

(54) PROCESS FOR THE PREPARATION OF 4-AMINO-3-CHLORO-5-FLUORO-6-(SUBSTITUTED) PICOLINATES

(71) Applicants: James M. Renga, Indianapolis, IN (US);
Yuanming Zhu, Carmel, IN (US);
Gregory T. Whiteker, Carmel, IN (US);
Christian T. Lowe, Westfield, IN (US)

(72) Inventors: Kim E. Arndt, Carmel, IN (US); James M. Renga, Indianapolis, IN (US);
Yuanming Zhu, Carmel, IN (US);
Gregory T. Whiteker, Carmel, IN (US);
Christian T. Lowe, Westfield, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 14/171,791

(22) Filed: Feb. 4, 2014

(65) Prior Publication Data

US 2014/0142317 A1    May 22, 2014

Related U.S. Application Data

(63) Continuation of application No. 13/356,669, filed on Jan. 24, 2012, now abandoned.

(60) Provisional application No. 61/435,966, filed on Jan. 25, 2011.

(51) Int. Cl.
| | | |
|---|---|---|
| C07D 213/803 | (2006.01) | |
| C07D 213/79 | (2006.01) | |
| C07D 213/81 | (2006.01) | |
| C07D 213/84 | (2006.01) | |

(52) U.S. Cl.
CPC .......... *C07D 213/803* (2013.01); *C07D 213/79* (2013.01); *C07D 213/81* (2013.01); *C07D 213/84* (2013.01)

(58) Field of Classification Search
None
See application file for complete search history.

(56) References Cited

U.S. PATENT DOCUMENTS

| | | |
|---|---|---|
| 3,803,159 A | 4/1974 | Torba |
| 6,297,197 B1 | 10/2001 | Fields |
| 6,784,137 B2 | 8/2004 | Balko |
| 7,314,849 B2 | 1/2008 | Balko |
| 7,432,227 B2 | 10/2008 | Balko |
| 7,498,468 B2 | 3/2009 | Balko et al. |

FOREIGN PATENT DOCUMENTS

WO PCT/US2012/022285    3/2014

*Primary Examiner* — Zinna Northington Davis
(74) *Attorney, Agent, or Firm* — Michael R. Asam

(57) ABSTRACT

4-Amino-3-chloro-5-fluoro-6-(substituted)picolinates are conveniently prepared from 3,4,5,6-tetrachloropicolinonitrile by a series of steps involving fluorine exchange, amination, halogen exchange and hydrolysis, esterification and transition metal assisted coupling.

2 Claims, No Drawings

US 9,067,890 B2

PROCESS FOR THE PREPARATION OF 4-AMINO-3-CHLORO-5-FLUORO-6-(SUBSTITUTED) PICOLINATES

CROSS REFERENCE TO RELATED APPLICATIONS

This application is a continuation of U.S. Ser. No. 13/356,669, filed Jan. 24, 2012, now abandoned, which claims the benefit of U.S. Provisional Patent Application Ser. No. 61/435,966 filed Jan. 25, 2011.

FIELD OF THE INVENTION

The present invention concerns a process for the preparation of 4-amino-3-chloro-5-fluoro-6-(substituted)picolinates. More particularly, the present invention concerns a process for the preparation of 4-amino-3-chloro-5-fluoro-6-(substituted)picolinates in which the 5-fluoro substituent is introduced by a halogen exchange early in the process scheme.

BACKGROUND OF THE INVENTION

U.S. Pat. No. 6,297,197 B1 describes inter alia certain 4-amino-3-chloro-5-fluoro-6-(alkoxy or aryloxy)picolinate compounds and their use as herbicides. U.S. Pat. Nos. 6,784,137 B2 and 7,314,849 B2 describe inter alia certain 4-amino-3-chloro-5-fluoro-6-(aryl)picolinate compounds and their use as herbicides. U.S. Pat. No. 7,432,227 B2 describes inter alia certain 4-amino-3-chloro-5-fluoro-6-(alkyl)picolinate compounds and their use as herbicides. Each of these patents describes the manufacture of 4-amino-3-chloro-5-fluoro-6-(substituted)picolinate starting materials by fluorination of the corresponding 5-(unsubstituted)picolinates with 1-(chloromethyl)-4-fluoro-1,4-diazoniabicyclo[2.2.2]octane bis(tetrafluoroborate). It would be advantageous to produce 4-amino-3-chloro-5-fluoro-6-(substituted)picolinates without having to rely on direct fluorination of the 5-position of the picolinate with an expensive fluorinating agent like 1-(chloromethyl)-4-fluoro-1,4-diazoniabicyclo[2.2.2]octane bis(tetrafluoroborate).

SUMMARY OF THE INVENTION

The present invention concerns a process for the preparation of 4-amino-3-chloro-5-fluoro-6-(substituted)picolinates from 3,4,5,6-tetrachloropicolinonitrile. More particularly, the present invention concerns a process for the preparation of a 4-amino-3-chloro-5-fluoro-6-(substituted)picolinate of the Formula I

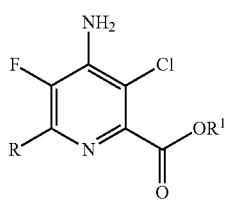

I wherein

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy;

$R^1$ represents $C_1$-$C_{12}$ alkyl or an unsubstituted or substituted $C_7$-$C_{11}$ arylalkyl; which comprises the following steps:

a) fluorinating 3,4,5,6-tetrachloropicolinonitrile (Formula A)

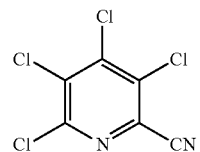

A with a source of fluoride ion to produce 3-chloro-4,5,6-trifluoropicolinonitrile (Formula B)

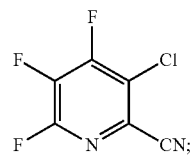

B b) aminating 3-chloro-4,5,6-trifluoro-2-picolinonitrile (Formula B) with ammonia to produce 4-amino-3-chloro-5,6-difluoropicolinonitrile (Formula C)

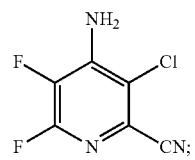

C c) exchanging the fluoro substituent in the 6-position of 4-amino-3-chloro-5,6-difluoropicolinonitrile (Formula C) with hydrogen bromide (HBr), hydrogen chloride (HCl) or hydrogen iodide (HI) and hydrolyzing the nitrile to produce a 4-amino-3-chloro-5-fluoro-6-halopicolinamide of Formula D

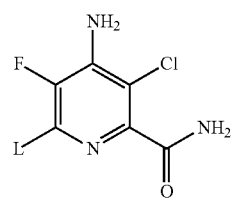

D wherein L is Br, Cl or I;

d) esterifying the 4-amino-3-chloro-5-fluoro-6-halopicolinamide of Formula D with a strong acid and an alcohol ($R^1OH$) to produce a 4-amino-3-chloro-5-fluoro-6-halopicolinate of Formula E

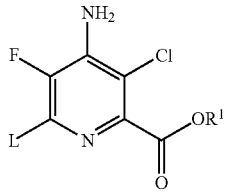

wherein L and $R^1$ are as previously defined; and e) coupling the 4-amino-3-chloro-5-fluoro-6-halopicolinate of Formula E with an aryl, alkyl or alkenyl metal compound of the Formula F R-Met        F wherein R is as previously defined and Met represents Zn-halide, Zn—R, tri-($C_1$-$C_4$ alkyl)tin, copper, or B($OR^2$)($OR^3$), where $R^2$ and $R^3$ are independent of one another, hydrogen, $C_1$-$C_4$ alkyl, or when taken together form an ethylene or propylene group in the presence of a transition metal catalyst to produce the 4-amino-3-chloro-5-fluoro-6-(substituted)picolinate of Formula I.

The steps a) through e) are typically performed as depicted in Scheme I.

Scheme I

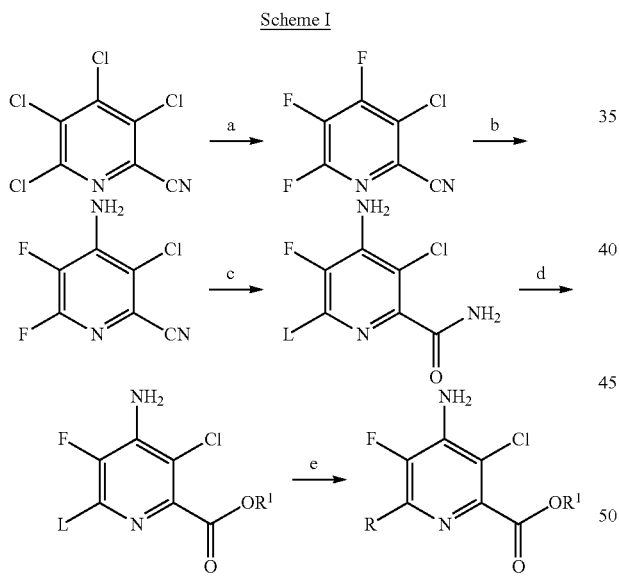

Another aspect of the present invention is the novel intermediates produced during the present process, viz., compounds of the formula:

a)

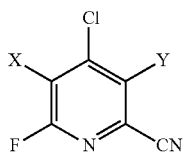

wherein X and Y independently represent F or Cl;

b)

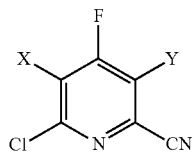

wherein X and Y independently represent F or Cl with the proviso that at least one of X and Y are F;

c)

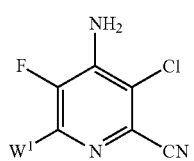

wherein $W^1$ represents F, Cl, Br or I;

d)

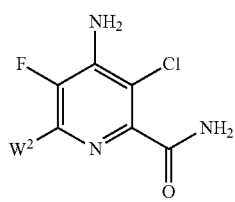

wherein $W^2$ represents Cl, Br or I; or e)

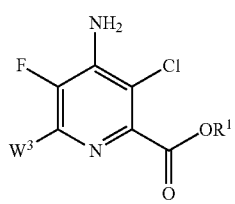

wherein $R^1$ represents $C_1$-$C_{12}$ alkyl or an unsubstituted or substituted $C_7$-$C_{11}$ arylalkyl and $W^3$ is Br or I.

DETAILED DESCRIPTION OF THE INVENTION

The terms "alkyl," "alkenyl" and "alkynyl," as well as derivative terms such as "alkoxy," "acyl," "alkylthio" and "alkylsulfonyl," as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "arylalkyl," as used herein, refers to a phenyl substituted alkyl group having a total of 7 to 11 carbon atoms, such as benzyl (—$CH_2C_6H_5$), 2-methylnaphthyl (—$CH_2C_{10}H_7$) and 1- or 2-phenethyl (—$CH_2CH_2C_6H_5$ or —CH(CH$_3$)C$_6$H$_5$). The phenyl group may itself be unsubstituted or substituted with one or more substituents independently selected from halogen, nitro, cyano, C$_1$-C$_6$ alkyl, C$_1$-C$_6$ alkoxy, halogenated C$_1$-C$_6$ alkyl, halogenated C$_1$-C$_6$ alkoxy, C$_1$-C$_6$ alkylthio, C(O)OC$_1$-C$_6$alkyl, or where two adjacent substituents are taken together as —O(CH$_2$)—O— wherein n=1 or 2, provided that the substituents are sterically compatible and the rules of chemical bonding and strain energy are satisfied.

Unless specifically limited otherwise, the term "halogen," as well as derivative terms such as "halo," refers to fluorine, chlorine, bromine and iodine.

The phenyl groups substituted with from 1 to 4 substituents independently selected from halogen, C$_1$-C$_4$ alkyl, C$_1$-C$_4$ haloalkyl, C$_1$-C$_4$ alkoxy or C$_1$-C$_4$ haloalkoxy may be of any orientation, but 4-substituted phenyl, 2,4-disubstituted phenyl, 2,3,4-trisubstituted phenyl, 2,4,5-trisubstituted phenyl, and 2,3,4,6-tetrasubstituted phenyl isomers are preferred.

The 4-amino-3-chloro-5-fluoro-6-(substituted)picolinates are prepared from 3,4,5,6-tetrachloropicolinonitriles by a series of steps involving fluorine exchange, amination, reaction with HCl, HBr or HI, hydrolysis, esterification and transition metal assisted coupling. The individual steps may be performed in different sequences.

The 3,4,5,6-tetrachloropicolinonitrile starting material is a known compound and is commercially available.

In the fluoride exchange reaction, the fluorinated picolinonitrile is prepared by reacting the corresponding chlorinated picolinonitrile with approximately one equivalent of fluoride ion source for each ring chlorine substituent to be exchanged.

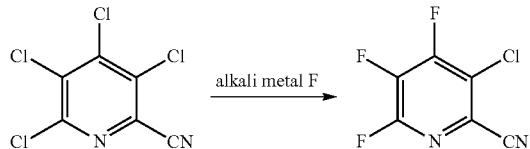 [SMILES: N#Cc1nc(Cl)c(Cl)c(Cl)c1Cl ; N#Cc1nc(F)c(F)c(F)c1Cl]

Typical fluoride ion sources are alkali metal fluorides which include sodium fluoride (NaF), potassium fluoride (KF) and cesium fluoride (CsF), with KF and CsF being preferred. Quaternary alkyl or aryl ammonium or phosphonium fluoride may also be used as a fluoride source or as an additive. Preferably, the reaction is carried out in a polar aprotic solvent or reaction medium such as, dimethylsulfoxide (DMSO), N-methylpyrrolidinone (NMP), N,N-dimethylformamide (DMF), hexamethylphosphoramide (HMPA) or sulfolane. The temperature at which the reaction is conducted is not critical but usually is from about 60° C. to about 180° C. and preferably from about 70° C. to about 80° C. Depending upon which solvent is employed in a particular reaction, the optimum temperature will vary. Generally speaking, the lower the temperature the slower the reaction will proceed. The present reaction is typically conducted in the presence of vigorous agitation sufficient to maintain an essentially uniformly dispersed mixture of the reactants.

In conducting the fluorination reaction, neither the rate nor the order of addition of the reactants is critical. Usually, the solvent and alkali metal fluoride are mixed before the chlorinated picolinonitrile is added to the reaction mixture. A typical reaction generally requires from about 2 to about 100 hours, preferably from 3 to 6 hours and is usually conducted at ambient atmospheric pressure.

While the exact amount of reactants is not critical, it is preferred to employ an amount of alkali metal fluoride which will supply at least an equimolar amount of fluorine atoms based on the number of chlorine atoms to be exchanged in the starting material, i.e., at least an equimolar amount of alkali metal fluoride. After the reaction is completed the desired product is recovered by employing standard separation and purification techniques such as distillation, crystallization or chromatography.

In a typical fluoride exchange, a mixture of products is obtained, including a significant amount of the over-fluorinated by-product 3,4,5,6-tetrafluoropicolinonitrile (Formula H).

H

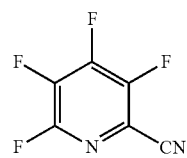

The ultimate yield of the desired 3-chloro-4,5,6-trifluoropicolinonitrile can be enhanced by isolating the over-fluorinated by-product 3,4,5,6-tetrafluoropicolinonitrile and recycling it to produce intermediates that can be subjected to the fluoride exchange reaction. This can be accomplished in several ways. Reaction of 3,4,5,6-tetrafluoropicolinonitrile with LiCl or reaction of 3,4,5,6-tetrafluoropicolinonitrile with an excess of 3,4,5,6-tetrachloropicolinonitrile or a combination of both, with or without solvents, leads to mixtures of chlorofluoropicolinonitriles where the 3-chloro isomers are useful as a starting material to form the desired product. Thus 3,4,5,6-tetrafluoropicolinonitrile can be heated with excess LiCl to produce a mixture of predominately 3,4,5-trichloro-6-fluoropicolinonitrile and 3,4,5,6-tetrachloropicolinonitrile. In another technique, reaction of the isolated 3,4,5,6-tetrafluoropicolinonitrile with an excess of 3,4,5,6-tetrachloropicolinonitrile in the presence of a phase-transfer catalyst produces a mixture consisting predominantly of monofluoro-trichloropicolinonitriles and difluoro-dichloropicolinonitriles. Finally, equal mixtures of isolated 3,4,5,6-tetrafluoropicolinonitrile and 3,4,5,6-tetrachloropicolinonitrile in the presence of a phase-transfer catalyst and from about 1 to about 3 equivalents of LiCl produces a mixture of predominately 3,4,5-trichloro-6-fluoropicolinonitrile and 3,4,5,6-tetrachloropicolinonitrile. These mixtures, consisting predominantly of monofluoro-trichloropicolinonitriles and/or difluorodichloropicolinonitriles, are useful in a fluorination reaction using an alkali metal fluoride to prepare 3-chloro-4,5,6-trifluoropicolinonitrile from 3,4,5,6-tetrafluoropicolinonitrile.

In a reverse halogen exchange reaction, 3,4,5,6-tetrafluoropicolinonitrile is heated with from about 5 to about 10 equivalents of LiCl, preferably with about 6 equivalents to produce a mixture of 4,5-dichloro-3,6-difluoropicolinonitrile (3,6-F$_2$—PN), 6-fluoro-3,4,5-trichloropicolinonitrile (6-F-PN) and 3,4,5,6-tetrachloropicolinonitrile (Cl$_4$-PN). The reaction can be carried out neat or in a polar aprotic solvent or reaction medium such as, DMSO, NMP, DMF, HMPA or sulfolane. It is often convenient to conduct the reaction in a solvent. The temperature at which the reaction is conducted is not critical but usually is from about 80° C. to about 200° C. and preferably from about 100° C. to about 150° C.

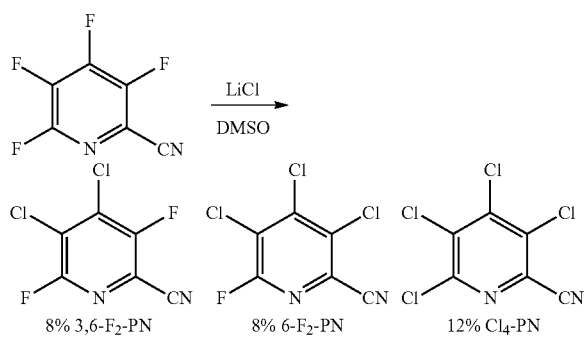

8% 3,6-F₂-PN     8% 6-F₂-PN     12% Cl₄-PN

About 90% or more of the mixture is useful to form 3-chloro-4,5,6-trifluoropicolinonitrile by recycling the mixture through the fluorine exchange reaction.

In the metathesis reaction in which fluoro and chloro groups are interchanged, the 3,4,5,6-tetrafluoropicolinonitrile is reacted with from 1 to about 3 equivalents of 3,4,5,6-tetrachloropicolinonitrile, preferably with about 2 equivalents of 3,4,5,6-tetrachloropicolinonitrile. The reaction can be carried out neat or in a polar aprotic solvent or reaction medium such as, DMSO, NMP, DMF, HMPA or sulfolane. It is often convenient to conduct the reaction without a solvent. The metathesis reaction is conducted in the presence of an additive. Additives include (a) quaternary phosphonium salts containing 10 or more carbon atoms and (b) macrocyclic polyethers commonly known as crown ethers. Suitable crown ether catalysts include, but are not limited to, 18-crown-6; dicyclohexano-18-crown-6; dibenzo-18-crown-6; 15-crown-S. Suitable quaternary phosphonium salts include the tetra-n-alkylphosphonium salts which are especially preferred. The temperature at which the reaction is conducted is not critical but usually is from about 80° C. to about 200° C. and preferably from about 150° C. to about 180° C.

In a typical metathesis reaction, for example, in which 1 equivalent of 3,4,5,6-tetrafluoropicolinonitrile is allowed to react with about 2 equivalents of 3,4,5,6-tetrachloropicolinonitrile, the following mixture of isomers can be obtained: 3,4,5,6-tetrachloropicolinonitrile (Cl₄-PN), 3,5-dichloro-4,6-difluoropicolinonitrile (4,6-F₂—PN), 3,4-dichloro-5,6-difluoropicolinonitrile (5,6-F₂—PN), 4,5-dichloro-3,6-difluoropicolinonitrile (3,6-F₂—PN), 6-fluoro-3,4,5-trichloropicolinonitrile (6-F-PN) and 4-fluoro-3,5,6-trichloropicolinonitrile (4-F-PN).

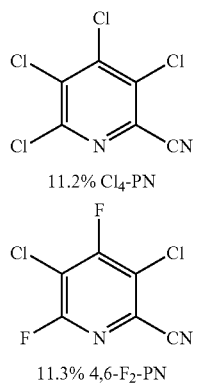

11.2% Cl₄-PN 11.3% 4,6-F₂-PN

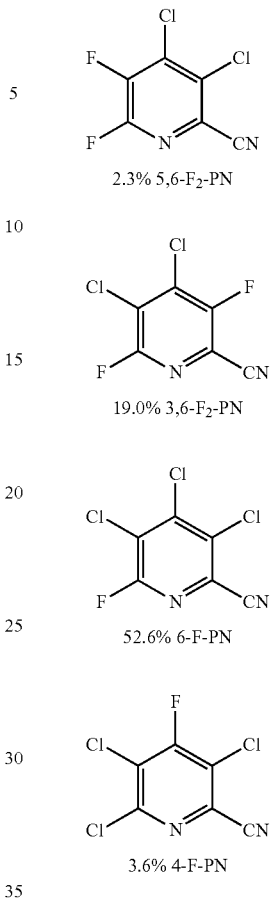

2.3% 5,6-F₂-PN 19.0% 3,6-F₂-PN 52.6% 6-F-PN 3.6% 4-F-PN

About 80% of the mixture is useful to form 3-chloro-4,5,6-trifluoropicolinonitrile by recycling the mixture through the fluorine exchange reaction.

In the combination of reverse halogen exchange reaction and the metathesis reactions, the 3,4,5,6-tetrafluoropicolinonitrile is allowed to react with from 1 to about 3 equivalents of 3,4,5,6-tetrachloropicolinonitrile, preferably with about 1 equivalent of 3,4,5,6-tetrachloropicolinonitrile and with from about 1 to about 4 equivalents of LiCl, preferably with from about 1.5 to about 2.5 equivalents. The reaction can be carried out neat or in a polar aprotic solvent or reaction medium such as, DMSO, NMP, DMF, HMPA or sulfolane. It is often convenient to conduct the reaction without a solvent. The metathesis reaction is conducted in the presence of an additive. Additives include (a) quaternary phosphonium salts containing 10 or more carbon atoms and (b) macrocyclic polyethers commonly known as crown ethers. Suitable crown ether catalysts include, but are not limited to, 18-crown-6; dicyclohexano-18-crown-6; dibenzo-18-crown-6; 15-crown-S. Suitable quaternary phosphonium salts include the tetra-n-alkylphosphonium salts which are especially preferred. The temperature at which the reaction is conducted is not critical but usually is from about 80° C. to about 200° C. and preferably from about 150° C. to about 180° C.

In a typical combination of the reverse halogen exchange and metathesis reactions, for example, 1 equivalent of 3,4,5,6-tetrafluoropicolinonitrile is allowed to react with about 1 equivalent of 3,4,5,6-tetrachloropicolinonitrile and 1.5 equivalents of LiCl, and the following mixture of isomers can be obtained:

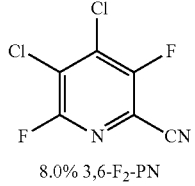

8.0% 3,6-F$_2$-PN

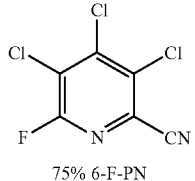

75% 6-F-PN

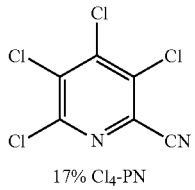

17% Cl$_4$-PN

About 92% of the mixture is useful to form 3-chloro-4,5,6-trifluoropicolinonitrile by recycling the mixture through the fluorine exchange reaction.

In the amination reaction, the 4-fluoropicolinonitrile is allowed to react with ammonia to replace the fluorine atom with an amino group.

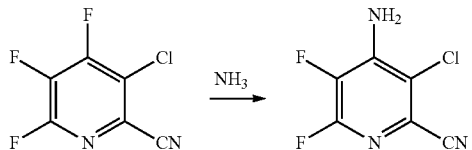

While only a stoichiometric amount of ammonia is required, it is often convenient to use a large excess of ammonia. It is often convenient to use the ammonia as both the reactant and the base to neutralize the hydrogen fluoride (HF) produced in the reaction. Alternatively, the ammonia can be in solution form, such as an aqueous solution of ammonium hydroxide. The reaction is carried out without a solvent or in an inert solvent. If a solvent is used, inert solvents include, but are not limited to, alcohols, ethers, esters, ketones, DMSO and aromatic solvents. The temperature at which the reaction is conducted is not critical but usually is from about 0° C. to about 45° C. and preferably from about 10° C. to about 30° C.

A typical reaction generally requires from about 0.5 to about 5 hours and is usually conducted at ambient atmospheric pressure. The desired product is recovered by employing standard separation and purification techniques.

In the halogen exchange and hydrolysis reaction, the 6-halopicolinamide is prepared by reacting the corresponding 6-fluoropicolinonitrile with at least two equivalents of a hydrogen halide.

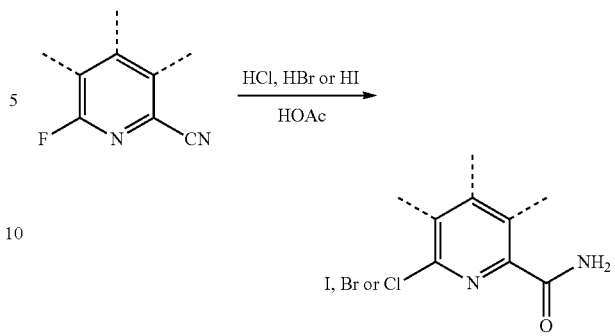

While only two equivalents of hydrogen halide are required, it is often convenient to use a large excess of the hydrogen halide. The reaction is carried out in an inert organic solvent, with C$_1$-C$_4$ alkanoic acids being especially preferred. The temperature at which the reaction is conducted is not critical but usually is from about 75° C. to about 150° C. and preferably from about 100° C. to about 130° C. The halogen exchange is conveniently conducted under pressure in a sealed vessel.

In conducting the halogenation and hydrolysis reactions, the 6-fluoropicolinonitrile can be heated with the hydrogen halide and alkanoic acid solvent in a sealed reactor. A typical reaction generally requires from about 0.5 to about 24 hours. The desired product is recovered by employing standard separation and purification techniques.

In the esterification reaction, the 2-picolinamide is reacted with an alcohol in the presence of a Bronsted acid or Lewis acid.

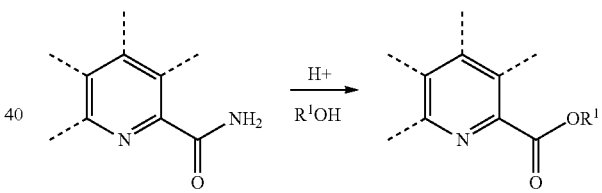

Bronsted acids include but are not limited to acids such as hydrochloric acid, sulfuric acid and phosphoric acid. Lewis acids include boron trifluoride, titanium tetrahalides, titanium tetraalkoxides, zinc halides, tin halides and phosphorus and antimony pentafluorides. Acids such as sulfuric acid or phosphoric acid are typically employed in stoichiometric amounts. The reaction is carried out in the C$_1$-C$_{12}$ alkyl alcohol or an unsubstituted or substituted C$_7$-C$_{11}$ arylalkyl alcohol of the desired ester. The reaction can be conveniently conducted in a sealed reactor if the reaction temperature is above the boiling temperature of the alcohol solvent.

In conducting the esterification, the 2-picolinamide or 2-picolinonitrile is added to a mixture of the alcohol and acid. Although the temperature of the reaction is not critical it is often heated fromo 80° C. to 140° C. for about 2 to 24 hours, preferably from 100° C. to 120° C. for 6 to 8 hours. The desired product is recovered by employing standard separation and purification techniques.

It is sometimes convenient to conduct the esterification step in conjunction with the workup of the halogen exchange step.

In the coupling reaction, a 6-halopicolinate is reacted with an aryl, alkyl or alkenyl metal compound where the metal is a Zn-halide, Zn—R, tri-($C_1$-$C_4$ alkyl)tin, copper, or B($OR^2$) ($OR^3$), where $R^2$ and $R^3$ are independent of one another, hydrogen, $C_1$-$C_4$ alkyl, or when taken together form an ethylene or propylene group, in the presence of a transition metal catalyst.

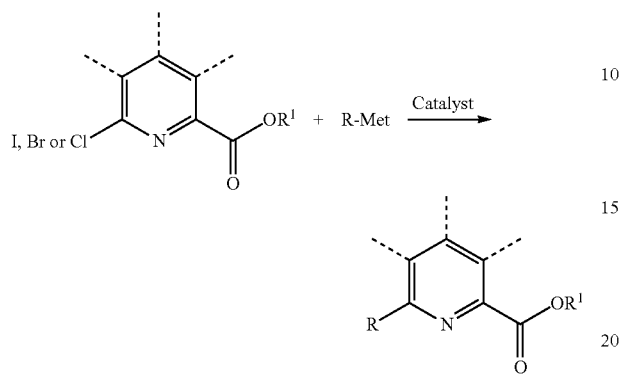

"Catalyst" is a transition metal catalyst, in particular a palladium catalyst such as palladium(II) acetate or dichlorobis(triphenylphosphine)palladium(II), or a nickel catalyst such as nickel(II) acetylacetonate or dichlorobis(triphenylphosphine)nickel(II). In addition, catalysts can be prepared in situ from metal salts and ligands, such as palladium(II) acetate and triphenylphosphine or nickel(II) chloride and triphenylphosphine. These in situ catalysts can be prepared by prior reaction of metal salt and ligand, followed by addition to the reaction mixture, or by separate addition of the metal salt and ligand directly to the reaction mixture.

Typically, coupling reactions are carried out in the absence of oxygen using an inert gas, such as nitrogen or argon. Techniques used to exclude oxygen from coupling reaction mixtures, such as sparging with inert gas, are well known to those skilled in the art. Examples of such techniques are described in *The Manipulation of Air-Sensitive Compounds*, $2^{nd}$ ed., D. F. Shriver, M. A. Drezdzon, Eds.; Wiley-Interscience, 1986. Sub-stoichiometric amounts of a catalyst are used, typically from about 0.0001 equivalents to 0.1 equivalents. Additional amounts of ligand may optionally be added to increase catalyst stability and activity. In addition, additives such as sodium carbonate, potassium carbonate, potassium fluoride, cesium fluoride and sodium fluoride are typically added to the coupling reaction. The coupling reaction generally requires from about 1 to about 5 equivalents of such additive, preferably from 1 to 2 equivalents. Water may optionally be added to the coupling reaction to increase the solubility of these additives. The coupling reaction generally requires from 1 to about 3 equivalents of an aryl, alkyl or alkenyl metal compound, preferably from 1 to 1.5 equivalents. The reaction is carried out in an inert solvent, such as toluene, THF, dioxane or acetonitrile. The temperature at which the reaction is conducted is not critical but usually is from about 25° C. to about 150° C. and preferably from about 50° C. to about 125° C. A typical reaction generally requires from about 0.5 to about 24 hours. No particular order of addition of reactants is typically required. It is often operationally simpler to combine all reactants except the catalyst and then deoxygenate the reaction solution. Following deoxygenation, the catalyst can be added to commence the coupling reaction.

When the Met portion of the aryl, alkyl or alkenyl metal compound is a Zn-halide, Zn—R, or copper, protection of reactive functional groups may be necessary. For example, if an amino substituent (—NHR or —$NH_2$) is present, protection of these reactive groups may be required. A variety of groups are known in the art for protection of amino groups from reaction with organometallic reagents. Examples of such protecting groups are described in *Protective Groups in Organic Synthesis*, $3^{rd}$ ed., T. W. Greene, P. G. M. Wuts, Eds.; Wiley-Interscience, 1999. The choice of which metal to use in R-Met is influenced by a number of factors, such as cost, stability, reactivity and the need to protect reactive functional groups.

The products obtained by any of these processes, can be recovered by conventional means, such as evaporation or extraction, and can be purified by standard procedures, such as by recrystallization or chromatography.

The following examples are presented to illustrate the invention.

EXAMPLES

Fluorine Exchange

Example 1a

3-Chloro-4,5,6-trifluoropicolinonitrile

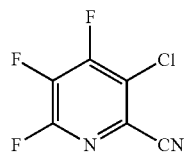

A 5-liter (L) mechanically stirred flask under nitrogen was charged with DMSO (3820 milliliters (mL)), powdered potassium carbonate ($K_2CO_3$; 42 grams (g)) and finely milled cesium fluoride (CsF; 1510 g). DMSO (approximately 1 L) was removed by distillation at 75-80° C. (3.5 mmHg, 0.46 kPa). The slurry was cooled to 55° C. under nitrogen before the addition of finely milled 3,4,5,6-tetrachloropicolinonitrile (685 g). The addition was conducted over a 15 minute (min) period while cooling to keep the reaction temperature below 74° C. The temperature was held at 65-70° C. under a slow nitrogen stream for 4 hours (h). The reaction mixture was cooled to about 40-50° C. and poured into a mixture of ice water ($H_2O$; 15 L) and diethyl ether ($Et_2O$; 3 L). After the organic phase was separated, the aqueous phase was extracted with $Et_2O$ (2×2 L). The organic extracts were combined, dried over magnesium sulfate ($MgSO_4$), filtered and concentrated by distillation at atmospheric pressure to give the crude product mixture (469 g) as light brown oil. This oil was combined with additional material prepared similarly to give a total of 1669 g of crude product. This oil was distilled under vacuum using a 30 tray Oldershaw column at a temperature range between 80-90° C. with fractions collected at 63, 13 and 2 mm Hg (8.4, 1.7 and 0.27 kPa). The material collected at 13 mm gave 457 grams (22% yield) of a solid that was a 93/7 mixture of two chlorotrifluoropicolinonitriles. This solid was recrystallized at 5° C. from a mixture of hexane (420 g) and $Et_2O$ to give 3-chloro-4,5,6-trifluoropicolinonitrile (354 grams, 98% purity) as fine white needles. A small sample was recrystallized a second time to 99.7% purity by gas chromatography (GC): mp 41.5-43° C.; $^{19}F$ NMR (376 MHz, $CDCl_3$) δ −78.1 (t, $J_{F-F}$=23.1 Hz, F6), −114.2 (dd, $J_{F-F}$=18.5, 22.5 Hz, F4), −149.3 (dd, $J_{F-F}$=18.2, 22.6 Hz, F5); $^{13}C\{^1H\}$ NMR (101

MHz, CDCl$_3$) δ 154.5 (ddd, J$_{F-C}$=270, 11, 7 Hz, C4), 151.3 (ddd, J$_{F-C}$=247, 13, 5 Hz, C6), 138.0 (ddd, J$_{F-C}$=279, 31, 13 Hz, C5), 124.7 (ddd, J$_{F-C}$=16, 6, 2 Hz, C3), 124.4 (ddd, J$_{F-C}$=16, 7, 2 Hz, C2), 112.2 (s, CN); EIMS m/z 192 ([M]$^+$). Anal. Calcd for C$_6$ClF$_3$N$_2$: C, 37.43; N, 14.55. Found: C, 36.91; N; 14.25.

The first part of the distillation (63 mm Hg, 8.4 kPa) gave pure 3,4,5,6-tetrafluoropicolinonitrile (525 g, 24%) as a colorless oil: $^{19}$F NMR (376 MHz, CDCl$_3$) δ −77.6 (t, J$_{F-F}$=23.8 Hz, F6), −133.7 (q, J$_{F-F}$=18.8 Hz, F4), −134.2 (ddd, J$_{F-F}$=24.2, 18.6, 10.1 Hz, F3), −145.3 (ddd, J$_{F-F}$=24.1, 18.2, 10.2 Hz, F5); $^{13}$C{$^1$H} NMR (101 MHz, CDCl$_3$) δ 150.4 (dm, J$_{F-C}$=272 Hz, C3), 148.5 (ddd, J$_{F-C}$=245, 12, 4 Hz, C6), 147.3 (dm, J$_{F-C}$=270 Hz, C4), 138.6 (ddd, J$_{F-C}$=280, 33, 11 Hz, C5), 113.4 (m, C2), 110.20 (s, CN).

The third part of the distillation (2 mm Hg, 0.27 kPa) gave 3,5-dichloro-4,6-difluoropicolinonitrile (48 g, 98% purity) as a white solid: mp 78-79° C.; $^{19}$F NMR (376 MHz, CDCl$_3$) δ −63.65 (d, J$_{F-F}$=18.7 Hz, F6), −92.52 (d, J$_{F-F}$=18.5 Hz, F4); $^{13}$C{$^1$H} NMR (101 MHz, CDCl$_3$) δ 162.6 (dd, J$_{F-C}$=269, 6 Hz, C4), 157.8 (dd, J$_{F-C}$=245, 5 Hz, C6), 127.6 (dd, J$_{F-C}$=17, 3 Hz, C3), 123.5 (dd, J$_{F-C}$=18, 6 Hz, C2), 112.4 (dd, J$_{F-C}$=36, 21 Hz, C5), 112.3 (CN).

Example 1b

Reverse Halogen Exchange Reaction of 3,4,5,6-tetrafluoropicolinonitrile with Lithium chloride

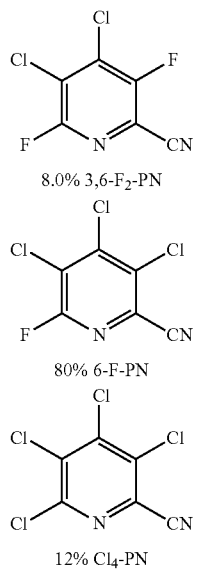

A mixture of 3,4,5,6-tetrafluoropicolinonitirile (17 g, 0.1 mole (mol)) and dry LiCl (25.4 g, 0.6 mol) was heated in dry DMSO (200 mL). The reaction was monitored by GC analysis of aliquots extracted into Et$_2$O from H$_2$O. Initially the reaction was heated to 120° C. and all of the LiCl dissolved. After 5 min at 120° C., all of the starting material and the chlorotrifluoro-PN isomers were consumed to give a mixture of 3,6-F$_2$—PN (83%) and 6-F-PN (14%). The temperature of the reaction was raised to 135° C. and after a total of 75 min was analyzed by GC. The mixture was determined to be a 8:80:12 mixture of 3,6-F$_2$—PN/6-F-PN/Cl$_4$-PN.

Example 1ca

Metathesis of 3,4,5,6-tetrafluoropicolinonitrile

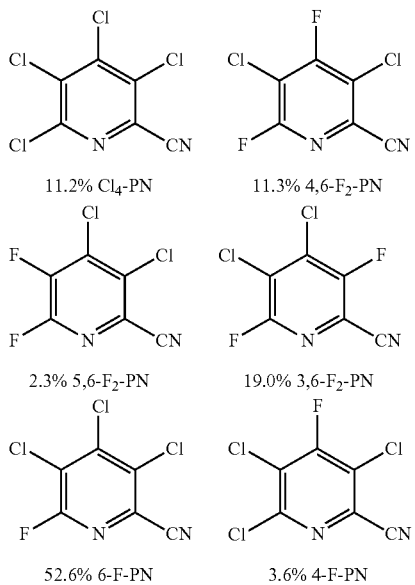

A mixture of 3,4,5,6-tetrachloropicolinonitrile (16.1 g, 66 millimoles (mmol)) and 3,4,5,6-tetrafluoropicolinonitrile (5.9 g, 33 mmol) were heated to 160° C. under nitrogen to form a solution. To this stirred solution was added tetrabutyl phosphonium chloride (Bu$_4$PCl; 0.36 g, 1.2 mmol), and the solution was held at 160° C. for 1 h. An aliquot was dissolved in methylene chloride (CH$_2$Cl$_2$) and passed through a short pad of silica gel before GC analysis. The profile of halogenated picolinonitriles was: 11.2% Cl$_4$-PN; 11.3% 4,6-F$_2$—PN; 2.3% 5,6-F$_2$—PN; 19% 3,6-F$_2$—PN; 52.6% 6-F-PN and 3.6% 4-F-PN. About 80% of the mixture is useful in the halogen exchange reaction to produce 3-chloro-4,5,6-trifluoropicolinonitrile.

Example 1cb

Recycle from Metathesis of 3,4,5,6-Tetrafluoropicolinonitrile

A reaction flask fitted with a short path distillation head was charged with finely milled CsF (35.1 g, 0.23 mol) and dry DMSO (175 mL). The reactor was stirred and heated to 70-75° C. under vacuum (0.1 mm) until DMSO (75 mL) was distilled off. This slurry was cooled to 50° C. under nitrogen, and the molten reaction mixture from above (21.7 g) was added. The reaction mixture was heated to 70° C. for 2.5 h with good stirring. A diethyl ether extract of an aliquot added to water was checked by GC and found to contain: 61% 3,4,5,6-tetrafluoropicolinonitrile; 31% 3-chloro-4,5,6-trifluoropicolinonitrile; 3.4% 5-chloro-3,5,6-trifluoropicolinonitrile and 4.8% 3,5-dichloro-4,6-difluoropicolinonitrile. This compares favorably to a typical crude GC purity of 38-42% when a similar reaction is conducted starting with pure 3,4,5,6-tetrachloropicolinonitrile.

Example 1d

LiCl Assisted Metathesis of 3,4,5,6-tetrafluoropicolinonitrile

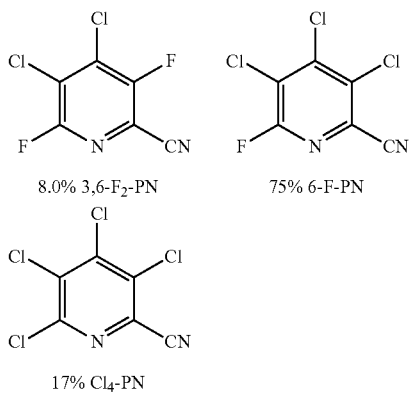

A mixture of 3,4,5,6-tetrachloropicolinonitrile (12.2 g, 50 mmol) and 3,4,5,6-tetrafluoropicolinonitrile (8.8 g, 50 mmol) were heated to 160° C. under nitrogen to achieve a clear solution. To this was added Bu$_4$PCl (0.36 g, 1.2 mmol). The reaction solution was held at 160° C. for 15 min before adding dry LiCl (4.2 g, 0.1 mol). After 60 min more LiCl (2.2 g, 50 mmol) was added, and the reaction mixture was stirred for 11 h. GC analysis of an ether extract from water showed an 8:75:17 mixture of 3,6-F$_2$—PN/6-F-PN/Cl$_4$-PN.

Amination

Example 2

4-Amino-3-chloro-5,6-difluoropicolinonitrile

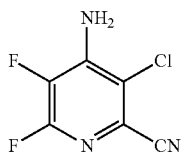 [SMILES: N#Cc1nc(F)c(F)c(N)c1Cl]

A solution of 3-chloro-4,5,6-trifluoropicolinonitrile (200 g) in ethyl acetate (EtOAc; 3 L) was cooled to 10° C. To this was slowly added 14% aqueous ammonium hydroxide (NH$_4$OH; 1296 g) keeping the temperature between 18-23° C. The aqueous solution was separated from the organic solution. The organic phase was washed sequentially with a 50/50 solution of aqueous saturated NaCl and water (500 mL) and saturated NaCl solution (250 mL). The organic phase was concentrated under vacuum at 50° C. to about 500 mL volume as the product crystallized out. To this slurry was added heptane (1 L), and the remaining EtOAc was removed under vacuum to give the final slurry. The solids were collected by filtration. This solid was washed with pentane and dried under vacuum to give 4-amino-3-chloro-5,6-difluoropicolinonitrile (173.8 g, 90%, 99.6% purity) as a white crystalline solid: mp 190-191.5° C.; $^{13}$C{$^1$H} NMR (101 MHz, DMSO-d$_6$) δ 150.03 (dd, J=232.4, 12.5 Hz, C6), 144.29 (dd, J=11.4, 6.9 Hz, C4), 133.72 (dd, J=257.9, 30.8 Hz, C5), 122.14 (dd, J=19.6, 4.9 Hz, C2), 119.31 (s, C3), 114.25 (s, CN); $^{19}$F NMR (376 MHz, DMSO-d$_6$) δ −91.24 (d, J=24.2 Hz), −154.97 (d, J=24.2 Hz); EIMS m/z 189 ([M]$^+$). Anal. Calcd for C$_6$H$_2$ClF$_2$N$_3$: C, 38.02; H, 1.06; N, 22.17. Found: C. 37.91; H. 1.00; 22.02.

Halogen Exchange, Hydrolysis and Esterification

Example 3

4-Amino-6-bromo-3-chloro-5-fluoropicolinamide and Methyl 4-amino-6-bromo-3-chloro-5-fluoropicolinate

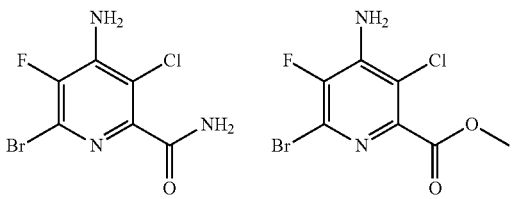

A mixture of 4-amino-3-chloro-5,6-difluoropicolinonitrile (70 g, 0.37 mol) and 33%

HBr in acetic acid (700 mL) was heated to 120° C. in a sealed, stirred reaction vessel for 2 h. After cooling to room temperature, the supernatant was separated from a large amount of a tan solid and concentrated under vacuum to give a tacky dark residue. This residue was taken into methyl alcohol (600 mL) and added back to the tan solids that remained in the pressure reactor. To this mixture was slowly added concentrated sulfuric acid (H$_2$SO$_4$; 40 g, 0.41 mol), and the reactor was again sealed and heated to 110° C. for 6 h. The cooled reaction mixture was slowly poured into saturated aqueous sodium carbonate (2 L) and Et$_2$O (1 L). The ether extract was dried over MgSO$_4$, filtered and concentrated to a tan solid. This solid was purified by column chromatography to give methyl 4-amino-6-bromo-3-chloro-5-fluoropicolinate (78 g, 75%) as fine white crystals: mp 119-120° C.; $^1$H NMR (400 MHz, CDCl$_3$) δ 3.97; $^{13}$C{$^1$H} NMR (101 MHz, DMSO-d$_6$) δ 163.54 (s, C=O), 144.63 (d, J=256.3 Hz, C5), 142.60 (d, J=4.9 Hz, C2), 140.55 (d, J=13.6 Hz, C4), 125.61 (d, J=21.0 Hz, C6), 116.65 (s, C3), 53.2 (s, OMe); $^{19}$F NMR (376 MHz, CDCl$_3$) δ −128.86; EIMS m/z 284 (Mr). Anal. Calcd for C$_7$H$_5$BrClFN$_2$O$_2$: C, 29.66; H, 1.78; N, 9.88. Found: C, 30.03; H, 1.80; N, 9.91.

Also isolated by column chromatography was 4-amino-6-bromo-3-chloro-5-fluoropicolinamide (200 mg) as a light tan solid: mp 215° C. dec; $^{13}$C{$^1$H}NMR (101 MHz, DMSO-d$_6$) δ 165.64 (s, C=O), 148.02 (d, J=4.8 Hz, C2), 142.31 (d, J=233.2 Hz, C5), 141.86 (d, J=14.0 Hz, C4), 124.13 (d, J=19.9 Hz, C6), 112.55 (d, J=2.1 Hz, C3); $^{19}$F NMR (376 MHz, DMSO-d$_6$) δ −131.56; EIMS m/z 269 ([M]$^+$). Anal.

Calcd for $C_6H_4BrClFN_3O$: C, 26.84; H, 1.50; N, 15.65. Found: C, 26.95; H, 1.52; N, 15.16.

Coupling

Example 4

Methyl 4-amino-3-chloro-5-fluoro-6-(4-chloro-2-fluoro-3-methoxy-phenyl)picolinate

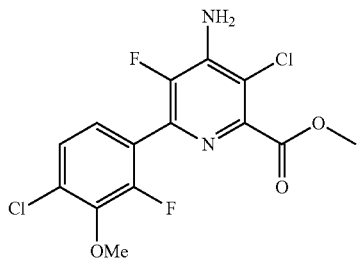 [SMILES: COC(=O)c1nc(-c2ccc(Cl)c(OC)c2F)c(F)c(N)c1Cl]

A stream of nitrogen was passed through a colorless mixture of methyl 4-amino-6-bromo-3-chloro-5-fluoropicolinate (2.8 g, 10 mmol) and 2-(4-chloro-2-fluoro-3-methoxyphenyl)-1,3,2-dioxaborinane (3.2 g, 13 mmol) in acetonitrile ($CH_3CN$; 40 mL) and KF (1.7 g, 30 mmol) in $H_2O$ (20 mL) while heating to 50° C. (20-30 min). Dichloro-bis(triphenylphosphine)palladium(II) ($PdCl_2(PPh_3)_2$; 140 mg, 0.2 mmol) was added, and the mixture was heated to 65° C. The reaction was monitored by HPLC and was complete after 5 h. The reaction mixture was filtered hot through a short pad of Celite then was diluted with $H_2O$ (20 mL) and allowed to cool. The product was collected by filtration. The light tan solid was dried under vacuum to give methyl 4-amino-3-chloro-6-(4-chloro-2-fluoro-3-methoxyphenyl)-5-fluoropicolinate (2.6 g, 72%): mp 169-170.5° C.; $^1H$ NMR (400 MHz, DMSO-$d_6$) δ 7.48 (d, J=8.4 Hz, 1H), 7.32 (t, J=7.7 Hz, 1H), 7.15 (s, 2H), 3.96 (s, 3H), 3.90 (s, 3H); $^{13}C\{^1H\}$ NMR (101 MHz, DMSO-$d_6$) δ 164.85 (s), 153.11 (d, J=252.5 Hz), 146.29 (s), 144.52 (d, J=4.3 Hz), 143.74 (s), 142.75 (dd, J=227.1, 14.0 Hz), 136.38 (d, J=13.4 Hz), 128.58 (d, J=3.2 Hz), 125.87 (s), 125.54 (d, J=3.5 Hz), 122.89 (dd, J=13.8, 4.0 Hz), 113.01 (d, J=3.0 Hz), 61.61 (d, J=4.2 Hz), 52.70 (s); ESIMS m/z 364 ([M+H]$^+$). Anal. Calcd for $C_{14}H_{10}Cl_2F_2N_2O_3$: C, 46.30; H, 2.78; N, 7.71. Found: C, 46.60; H, 2.68; N, 7.51.

What is claimed is:

1. A process for the preparation of a 4-amino-3-chloro-5-fluoro-6-(substituted)picolinate of the Formula I

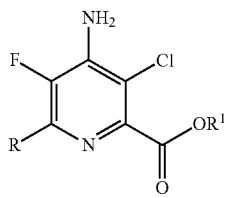

I wherein
R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy;
$R^1$ represents $C_1$-$C_{12}$ alkyl or an unsubstituted or substituted $C_7$-$C_{11}$ arylalkyl;
which comprises the following steps:
a) fluorinating 3,4,5,6-tetrachloropicolinonitrile (Formula A)

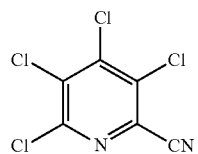

A with a source of fluoride ion to produce 3-chloro-4,5,6-trifluoropicolinonitrile (Formula B)

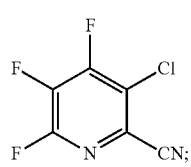

B b) aminating 3-chloro-4,5,6-trifluoro-2-picolinonitrile (Formula B) with ammonia to produce 4-amino-3-chloro-5,6-difluoropicolinonitrile (Formula C)

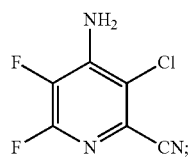

C c) exchanging the fluoro substituent in the 6-position of 4-amino-3-chloro-5,6-difluoropicolinonitrile (Formula C) with hydrogen bromide (HBr), hydrogen chloride (HCl) or hydrogen iodide (HI) and hydrolyzing the nitrile to produce a 4-amino-3-chloro-5-fluoro-6-halopicolinamide of Formula D

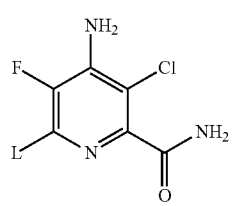

D wherein L is Br, Cl or I;
d) esterifying the 4-amino-3-chloro-5-fluoro-6-halopicolinamide of Formula D with a strong acid and an alcohol ($R^1$OH) to produce a 4-amino-3-chloro-5-fluoro-6-halopicolinate of Formula E

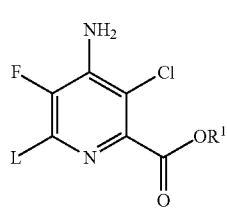

E wherein L and $R^1$ are as previously defined; and e) coupling the 4-amino-3-chloro-5-fluoro-6-halopicolinate of Formula E with an aryl, alkyl or alkenyl metal compound of the Formula F R-Met   F wherein R is as previously defined and Met represents Zn-halide, Zn-R, tri-($C_1$-$C_4$ alkyl)tin, copper, or B($OR^2OR^3$), where $R^2$ and $R^3$ are independent of one another, hydrogen, $C_1$-$C_4$ alkyl, or when taken together form an ethylene or propylene group in the presence of a transition metal catalyst to produce the 4-amino-3-chloro-5-fluoro-6-(substituted)picolinate of Formula I.

2. The process of claim 1, wherein the 4-amino-3-chloro-5-fluoro-6-(substituted)picolinate of the Formula I is methyl 4-amino-3chloro-5-fluoro-6-(4-chloro-2-fluoro-3methoxyphenyl)picolinate.

* * * * *